United States Patent [19]

Zeh

[11] Patent Number: 4,653,333
[45] Date of Patent: Mar. 31, 1987

[54] APPARATUS FOR SAMPLING TOXIC FLUIDS

[75] Inventor: Horst Zeh, Kolberger, Fed. Rep. of Germany

[73] Assignee: Wiederaufbereitungsanlage Karlsruhe Betriebsgesellschaft m.b.H., Eggenstein-Leopoldshafen, Fed. Rep. of Germany

[21] Appl. No.: 796,790

[22] Filed: Nov. 12, 1985

[30] Foreign Application Priority Data

Jan. 31, 1985 [DE] Fed. Rep. of Germany ....... 3503228

[51] Int. Cl.$^4$ .............................................. G01N 1/10
[52] U.S. Cl. ................................ 73/863.81; 73/864.31
[58] Field of Search .......... 73/863.81, 864.51, 864.31, 73/864.74, 863.85

[56] References Cited

U.S. PATENT DOCUMENTS

| | | | |
|---|---|---|---|
| 3,383,923 | 5/1968 | Conche et al. | 73/864.31 X |
| 4,000,654 | 1/1977 | Harris, Jr. | 73/863.81 |
| 4,395,164 | 7/1983 | Beltrop et al. | 73/864.31 |
| 4,512,203 | 4/1985 | Colame-Lonjean et al. | 73/863.81 |
| 4,516,436 | 5/1985 | Conche et al. | 73/864.31 X |
| 4,526,045 | 7/1985 | Reekie | 73/864.31 |
| 4,574,645 | 3/1986 | Allen et al. | 73/863.81 X |

FOREIGN PATENT DOCUMENTS 2642065 12/1977 Fed. Rep. of Germany .

*Primary Examiner*—Michael J. Tokar
*Assistant Examiner*—Tom Noland

[57] ABSTRACT

A sampling apparatus for taking samples of a toxic fluid from within a shielded chamber has a rotatable shaft which extends downwardly through the shielding wall and is provided at its front end within the chamber with a cavity adapted to receive sampling bottles supplied thereto and removed therefrom through supply and return pipes. A hollow needle is mounted on a needle head disposed in front of the shaft such that the needle can be inserted into a sampling bottle disposed in the shaft cavity and sample fluid can be injected into the bottle from the needle head to which the fluid is conducted by a supply line and from which it may be removed through a discharge line.

5 Claims, 5 Drawing Figures

APPARATUS FOR SAMPLING TOXIC FLUIDS

BACKGROUND OF THE INVENTION

The invention relates to a sampling apparatus for sampling radioactive or otherwise toxic compounds containing fluids.

Sampling arrangements are known (see German Pat. No. 2,642,065) which permit the extraction of samples from various process containers of a plant. Such sampling, however, takes place in especially equipped glove boxes into which the sampling bottles must be introduced and from which they must be removed after being filled.

It is the object of the present invention to provide a sampling arrangement of the given type which permits, however, direct sampling within the cell in which a process takes place and which can be operated through the cell walls behind which the processing equipment is installed.

SUMMARY OF THE INVENTION

A sampling apparatus for taking samples of a toxic fluid from equipment arranged within a chamber provided with shielding walls has a rotatable shaft which extends downwardly through the shielding wall and has at its front end within the chamber a cavity for the reception of sampling bottles supplied thereto and removed therefrom through bottle supply and return pipes. Adjacent the front end of the shaft and in axial alignment therewith there is arranged a needle head including a hollow needle projecting axially toward the shaft cavity such that the needle can be inserted into a bottle within the cavity when the shaft is moved axially for delivering the toxic fluid to the bottle from the needle head to which the fluid is conducted by a supply line and from which it may be removed through a discharge line.

Preferably, the bottle supply pipe extends to a location above the shaft end so that the bottle falls into the shaft cavity when the shaft is at the respective angular position. The shaft may then be moved forwardly such that the bottle receives the needle through which the fluid is then introduced into the bottle. After filling of the bottle, the shaft is retracted and rotated 180° such that the shaft cavity is open downwardly and the bottle falls into the return pipe through which the bottle is then moved away.

The sampling arrangement may include such a linearly movable sampling device for each sampling location. It can be used for all kinds of radiation and is installed into the cell wall so that special α-radiation containments or γ-radiation protective walls are not needed. Neither a bottle margin nor additional pneumatic transport tubes and all the equipment for the transfer of the bottles between the sampling arrangement and the pneumatic transport tubes are necessary with the arrangement according to the invention. The mechanism for the change-over of sampling bottles includes a guide structure which prevents damage to the bottles and injection needle. The needle is preferably arranged inclined upwardly at an angle of about 30° and is beveled so as to provide a self-locking cone; clogging as a result of crystallization of residual liquids is prevented. Filling of the sampling bottle and removal of air therefrom is performed by means of a needle with relatively large flow cross-section which permits also the handling of liquid-suspended matter and which facilitates filling of the sampling bottles.

SHORT DESCRIPTION OF THE DRAWINGS

Figure 3A:
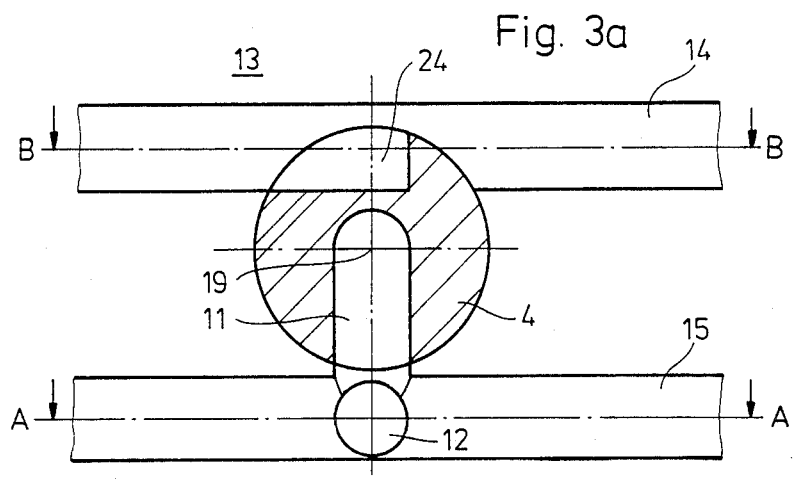
Figure 3B:
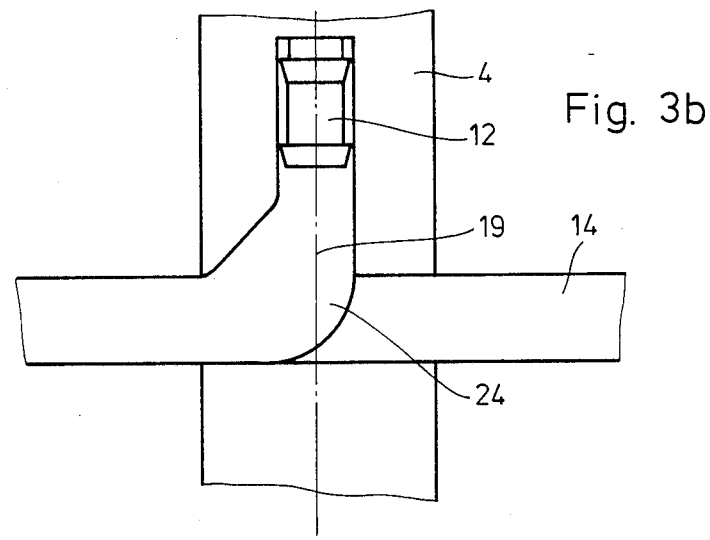
Figure 3C:
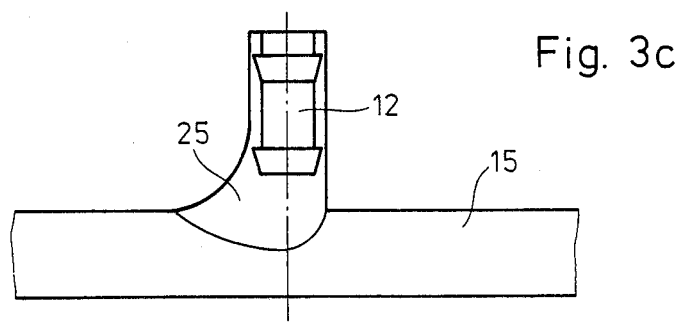

FIGS. 3A, 3B and 3C schematically show the sampling bottle exchange structure and the sampling procedure.

DESCRIPTION OF THE PREFERRED EMBODIMENT

Figure 1:
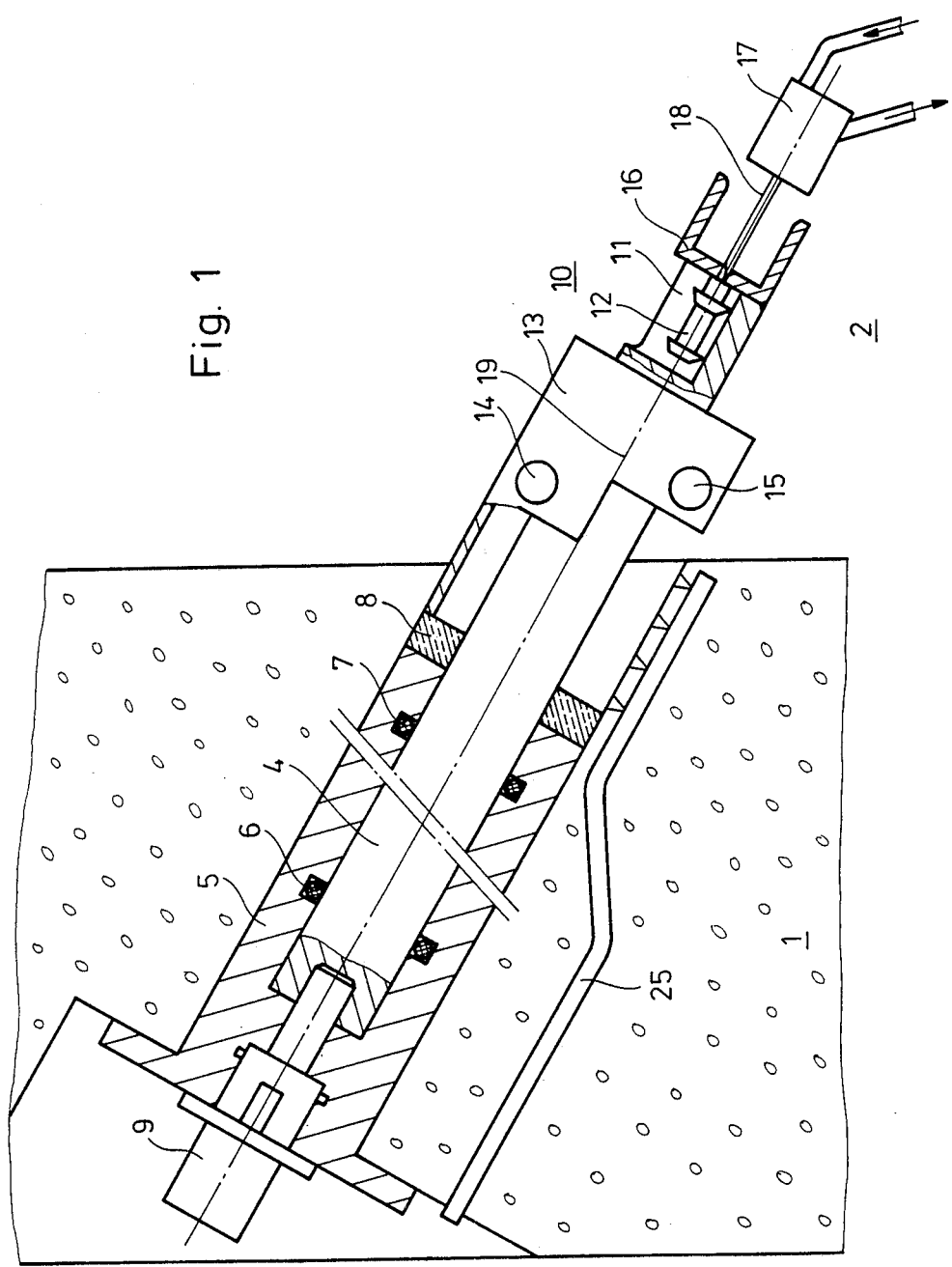
FIG. 1 is a cross-sectional view of the sampling arrangement.

FIG. 1 shows a cell wall 1 which separates a hot work area 2 from the operating room 3 for the process operators. Through the cell wall 1 inclined downwardly at an angle with regard to a horizontal line of about 30° extends a rotatable shaft 4 which is rotatably supported in a bearing sleeve 5 and sealed by means of O-rings 6 and 7 and by a lead ring 8. The shaft 4 is in the form of a spindle provided with a drive 9 consisting of an electric motor with infinitely variable speed adjustment and adapted to permit its operation against a stop.

The bearing sleeve 5 is sealed into the cell wall 1. Also extending through the cell wall 1 is a decontamination pipe 25 permitting the admission of a cleaning fluid for spraying and washing the front end 10 of the equipment within the cell 2.

At the front end 10, the shaft 4 is provided with special features: There is provided a cavity 11 for the reception of a sampling bottle 12 to be filled, an exchange structure 13 provided with supply and return pipes 14, 15 for the introduction and the removal of the sampling bottles 12 and a centering receiver 16 for the needle head 17.

The needle head 17 is disposed in alignment with the axis 19 and in front of the front end 10 of the shaft 4 so that, upon rotation and concurrent axial advance movement of the shaft 4, the sampling bottle 12 which has a fill opening at its front end is moved into the needle 18 or, after being filled, removed therefrom.

Figure 2:
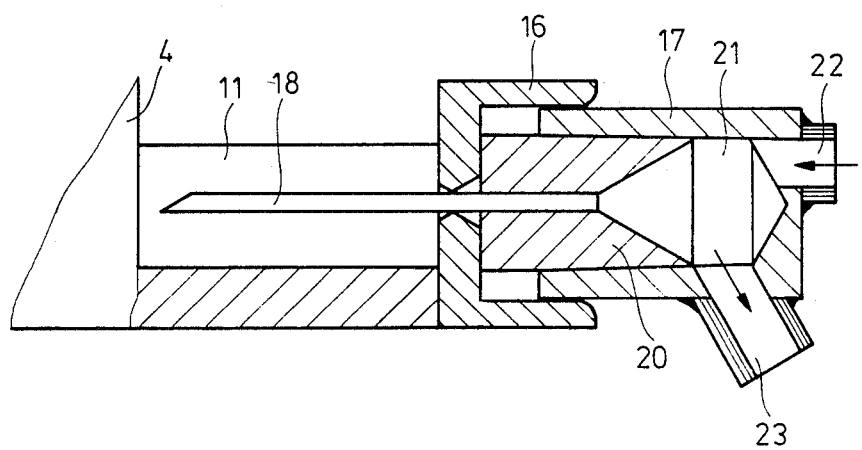
FIG. 2 shows the needle head.

The needle head 17 is shown in greater detail in FIG. 2. It essentially includes the hollow needle 18 which is mounted along the axis of a cork-type cone member 20 which itself is disposed in a needle head chamber 21. The chamber 21 has connected thereto supply and discharge lines 22 and 23 for the sample liquid which may be supplied through the supply line 22 over substantial distances (ca. 25 m) by an air lifting procedure, for example. The cone member 20 is removable from the needle head 17 simply by pulling it off with the aid of the shaft 4 by holding means, for example, by supplying to said cavity a body which engages the needle when it is pierced thereby. The needle head 17 is centered with respect to the shaft 4 and properly positioned with regard to the cavity 11 by the centering receiver 16. The inclined position of the needle head facilitates emptying of the needle after sampling since the residual liquid flows easier back through the chamber 21 into the discharge line 23.

Also, the sampling bottle 12 may be evacuated through the hollow needle 18 which improves the degree of bottle filling. The chamber 21 in the needle head 17 runs completely empty after discontinuation of the supply of sampling fluid thereto. A needle guide structure and the relatively large diameter of the needle, which results in good rigidity of the needle, provide for reliable and relatively long trouble-free operation. Sampling within the cell also provides for improved sampling fluid consistency. The transport of the sampling bottles 12 to and from the front end 10, that is, to and from the bottle exchange structure 13, is by way of the supply and return pipes 14 and 15. The exchange structure is shown in detail in FIGS. 3A–3C. The supply and return pipes 14 and 15 lead tangentially to the rotatable shaft 4. Within the pipes a single sampling bottle at a time is transported by a differential pressure as in pneumatic tubes. The sampling bottle 12, when arriving in tube 14 (FIG. 3A), is directed by a rounded guide structure 24 (FIG. 3B) into a position in alignment with the axis 19 of the rotatable shaft 4 and is then permitted to fall, either without delay or after rotation of the rotatable shaft 4 by 180° into the cavity 11. It is then properly positioned for the sampling procedure. After the sampling bottle is filled, the rotatable shaft 4, after being pulled back, is rotated by 180° such that it is positioned with the cavity open downwardly as shown in FIG. 3A, so that the sampling bottle 12 is first pulled from the needle 18 and is then transferred to the return pipe 15 which also has a rounded guide structure 25 by which the sampling bottle is turned 90° so as to be carried away in the pipe 15.

I claim:

1. A sampling apparatus for taking samples of a fluid including toxic materials from within a chamber enclosed by a shielding wall by introducing the fluid into a sampling bottle which is supplied to said apparatus through a supply pipe and remove it therefrom through a return pipe, said apparatus including:
   (a) a rotatable shaft extending through said shielding wall and having at its front end within said chamber a cavity for receiving said sampling bottle;
   (b) a hollow needle mounted on a needle head disposed in front of, and in axial alignment with, said shaft, said needle head having said supply and discharge lines connected thereto for supplying said fluid thereto;
   (c) a drive structure for rotating and for axially moving said shaft relative to said needle so as to cause said needle to enter a sampling bottle disposed in said cavity for delivering said fluid thereto; and
   (d) change-over means for supplying a bottle to said cavity and for removing it therefrom.

2. A sampling apparatus according to claim 1, wherein said rotatable shaft is a drive spindle mounted in a guide sleeve disposed in said shielding wall.

3. A sampling apparatus according to claim 1, wherein said cavity is radially open and said supply pipe extends to a position above said shaft cavity so as to be able to supply said bottle thereto, when said shaft is in the appropriate angular position and said return pipe extends to a position below said cavity such that a bottle can be delivered to said return pipe in the appropriate angular position of said shaft when the open end of said cavity is directed downwardly.

4. A sampling apparatus according to claim 1, wherein said shaft is disposed so as to extend through said chamber wall at an angle of about 30° from the horizontal.

5. A sampling apparatus according to claim 4, wherein said needle head is provided with a cone which is exchangeable by operation of said shaft and wherein said needle is inclined and extends upwardly through said cone, the lower end of said needle being in communication with a chamber in said needle head and the upper end of the needle being adapted to be inserted into a sampling bottle in said shaft cavity.

* * * * *